(12) United States Patent
Kwon et al.

(10) Patent No.: US 8,816,124 B2
(45) Date of Patent: Aug. 26, 2014

(54) ESTER-BASED REACTIVE PLASTICIZER FOR PLASTIC BONDED EXPLOSIVES

(71) Applicant: Agency for Defense Development, Daejeon (KR)

(72) Inventors: Young Hwan Kwon, Daegu (KR); Jin Seuk Kim, Daejeon (KR); Bum Jae Lee, Daejeon (KR); In Joo Bae, Daejeon (KR)

(73) Assignee: Agency for Defense Development, Daejeon (KR)

( * ) Notice: Subject to any disclaimer, the term of this patent is extended or adjusted under 35 U.S.C. 154(b) by 0 days.

(21) Appl. No.: 13/962,274

(22) Filed: Aug. 8, 2013

(65) Prior Publication Data

US 2014/0046091 A1  Feb. 13, 2014

(30) Foreign Application Priority Data

Aug. 9, 2012  (KR) .................. 10-2012-0087431

(51) Int. Cl.
  *C07C 69/52*  (2006.01)
  *C07C 69/606*  (2006.01)

(52) U.S. Cl.
  CPC .................. *C07C 69/606* (2013.01)
  USPC ........................ 560/222; 560/205

(58) Field of Classification Search
  CPC .................................. C07C 69/606
  See application file for complete search history.

(56) References Cited

U.S. PATENT DOCUMENTS

| 3,655,836 | A | 4/1972 | Dehm et al. |
| 4,108,926 | A | 8/1978 | Arnold et al. |
| 5,061,330 | A | 10/1991 | Reed, Jr. et al. |
| 5,520,756 | A | 5/1996 | Zeigler |
| 6,736,913 | B1 | 5/2004 | Hatch |

OTHER PUBLICATIONS

Database Caplus Chemical Abstracts Service, Columbus, Ohio, US; Database Accession No. 2011:704156, Abstract of Lee et al., New Trends in Research of Energetic Materials, Proceedings of the Seminar, 14th, Pardubice, Czech Republic, Apr. 13-15, 2011, vol. 2, 792-796. Editor(s): Pachman, Jiri; Selesovsky, Jakub; Matyas, Robert. Publisher: U.*

Advanced Organic Chemistry Part B: Reaction and Synthesis, Carey, Francis A., Sundberg, Richard J., Springer, 5th ed. 2007, pp. 664-668.*

Wypych, George, Handbook of Plasticizers, 2004, pp. 20-23, 66-67. Advance in Research of Energetic Plasticizers, Chemical Propellants & Polymeric Materials, 5(1), 2003, 9 pages.

* cited by examiner

*Primary Examiner* — Karl J Puttlitz (74) *Attorney, Agent, or Firm* — Harness, Dickey & Pierce, P.L.C.

(57) ABSTRACT

Disclosed is an energetic reactive plasticizer for a plastic bonded explosive (PBX), and specifically an energetic reactive plasticizer for PBX which has high performance and insensitiveness without a plasticizer leak by being bonded with a polymer binder for a plastic bonded explosive.

2 Claims, 6 Drawing Sheets

ESTER-BASED REACTIVE PLASTICIZER FOR PLASTIC BONDED EXPLOSIVES

CROSS-REFERENCE TO RELATED APPLICATION

This application claims the benefit and priority of Korean Patent Application No. 10-2012-0087431 filed Aug. 9, 2012. The entire disclosure of the above application is incorporated herein by reference.

TECHNICAL FIELD

The present invention relates to an energetic reactive plasticizer for a plastic bonded explosive, and specifically to an energetic reactive plasticizer for a plastic bonded explosive which has high performance and insensitiveness without a migration problem of a plasticizer by being bonded with a polymer binder for a plastic bonded explosive.

BACKGROUND ART

Currently, efforts to make energetic materials insensitive have been a significant issue in development of explosives and a propellant. As a part of such efforts, plastic bonded explosives (PBXs) having low sensitivity and improved mechanical properties while maintaining high energy properties have been developed. Such PBX now becomes an elementary component of high-energy explosives, polymeric binders and other additives used in a small amount such as a plasticizer or a stabilizer.

Currently, a polyurethane polymeric binder on the basis of a hydroxyl-terminated polybutadiene (HTPB) has been used as a widely applicable polymeric binder system, together with various additives so as to improve processability, mechanical properties and chemical stability. Although such polymeric binder shows excellent properties in making high-energy materials insensitive, it has been proposed that it generally disadvantageously reduces the energy density of PBX on the whole owing to its low energy potential. In this regard, many studies have been being made to increase the whole energy density through development of energetic binders and plasticizers containing energetic functional groups such as, for example, nitro ($C-NO_2$), nitrate ($O-NO_2$), nitramine ($N-NO_2$), azido ($-N_3$) and difluoroamino ($-NF_2$) and application thereof.

The term "energetic functional groups" as used herein has common and general meaning as used in the field of molecular explosives, i.e, referring to functional groups, when being applied to a molecular explosive or a plasticizer, known to contribute to the increase in the whole energy level of PBX to which the explosive or plasticizer were applied. Nitro ($C-NO_2$), nitrate ($O-NO_2$), nitramine ($N-NO_2$), azido ($-N_3$), difluoroamino ($-NF_2$) or the like as described above may be mentioned. The term "energetic" as used herein means that the whole energy level of a molecular explosive is more increased by any known methods comprising the introduction of such "energetic" functional groups.

However, those polymeric binders and plasticizers which comprise such energetic functional groups have problems such as low heat stability, non-compatibility with explosives and low processability. Therefore, it has been an important rising issue to ultimately achieve both high performance and insensitiveness in explosives. Further, when an energetic plasticizer is applied, an additional problem such as a migration of the energetic plasticizer from PBX occurs over a long period of time. Such migration of an energetic plasticizer involves further additional problems in PBX such as increase in sensitivity to impact and decrease in storage stability and long-term stability owing to deterioration in mechanical properties. Therefore, the realization of an explosive having both high performance and insensitiveness still has been an important matter to be achieved in this field of art.

When a highly energetic polymer which can satisfy both high performance and insensitiveness at the same time is prepared, it is anticipated to obtain a novel energy material which is combined with a molecular explosive and a binder and has an excellent performance and safety.

SUMMARY OF THE INVENTION

The present invention is to provide an energetic reactive plasticizer which can satisfy the high performance and insensitiveness required in the next-generation explosives without a plasticizer migration and thereby preventing various problems accompanied with such migration.

DETAILED DESCRIPTION OF THE INVENTION

PBX is majorly composed of a molecular explosive and a prepolymer and a curing agent for the formation of a binder, and additionally comprises other additives such as a plasticizer on necessary. All the components are introduced, mixed together and then loaded into a container for an explosive, this procedure of which is called a casting process. The prepolymer and the curing agent react in the container to form a binder while solidifying the components in the container.

The 'reactive plasticizer' is a high energy alkyne compound having low viscosity, which can be served as a plasticizer during mixing of PBX and attached to a polymer in a casting or curing process as above. The reactive plasticizer acts as a plasticizer in the preparation of PBX, and a part of or the whole plasticizer is bound into a binder by click reaction by itself in a curing process of the final preparation process.

The present inventors have found that by using a reactive plasticizer in a way of introducing high energy prepolymers in PBX preparation process, it acts as a plasticizer during the casting process, thereby solving the conventional viscosity problem and further it binds to a binder during a curing process, thereby reducing bleeding or migration of a plasticizer, and thus completed the present invention.

In other words, the present invention provides a novel reactive plasticizer having high energy potential by comprising a high energy functional group as well as a functional group which can react with a corresponding energetic prepolymer/a curing agent during a curing process in the preparation of a binder for PBX, thereby being bound to the high energy polymer binder as a side chain thereof.

The energetic reactive plasticizer according to the present invention binds with a side chain of a binder via a click reaction between azide and acetylene groups during the curing process. For such reaction, the energetic reactive plasticizer of the present invention comprises acetylene functional groups and the bond between the energetic functional group and the reactive functional group is an ester bond.

The ester-based energetic reactive plasticizer is an ester-based compound obtained according to the following reaction scheme 1:

(wherein, n=a natural number selected from 0-10).

As seen from the above reaction scheme 1, the reactive energetic plasticizer containing ester groups in the backbone chain is formed by esterification reaction between 2,2-dinitropropyl alcohol (DNP-OH) and an acetylene-containing carboxylic acid (AA). The esterification reaction may be carried out under the conventional reaction conditions known in this field of art and thus an energetic reactive plasticizer comprising ester groups in the backbone chain is synthesized as shown in the above reaction scheme 1.

The acetylene-containing carboxylic acid used in the above reaction includes for example, propiolic acid (n=0), 4-pentynoic acid (n=2) and 5-hexynoic acid (n=3), resulting in 2,2-dinitropropyl propiolate (DNPPE), 2,2-dinitropropyl-4-pentynoate (DNPPA) or 2,2-dinitropropyl-5-hexynoate (DNPHA), respectively.

EXAMPLES

Preparation Example 1

Synthesis and analysis of 2,2-dinitropropyl propiolate ester (DNPPE)

An energetic reactive plasticizer, DNPPE was synthesized as shown in the following reaction scheme 2 via esterification reaction of DNP-OH and propiolinic acid.

10 mL dichloroethylene, DNP-OH (5 g, 33.8 mmol), propiolinic acid (2.3 g, 37.2 mmol) and polymerized phosphoric acid (10.2 g) were placed into a 2-neck flask, and then the mixture was refluxed at 80° C. for 24 hours. The reactants were washed with dichloromethylene and NaHCO$_3$ (10%) solvent and then washed at least 5 times with distilled water. The solvent was removed under reduced pressure and the resultant was distilled at 80° C. under high vacuum condition, resulting in DNPPE.

The conformation of thus synthesized DNPPE was identified by the following methods. Firstly, $^1$H-NMR spectrum was used to identify the molecular structure of DNPPE, resulting in: $^1$H NMR (CDCl$_3$, d, ppm): 3.08 (1H, =C—H), 2.25 (3H, —CH$_3$), 5.02 (2H, —CH$_2$—COO—).

Figure 3:
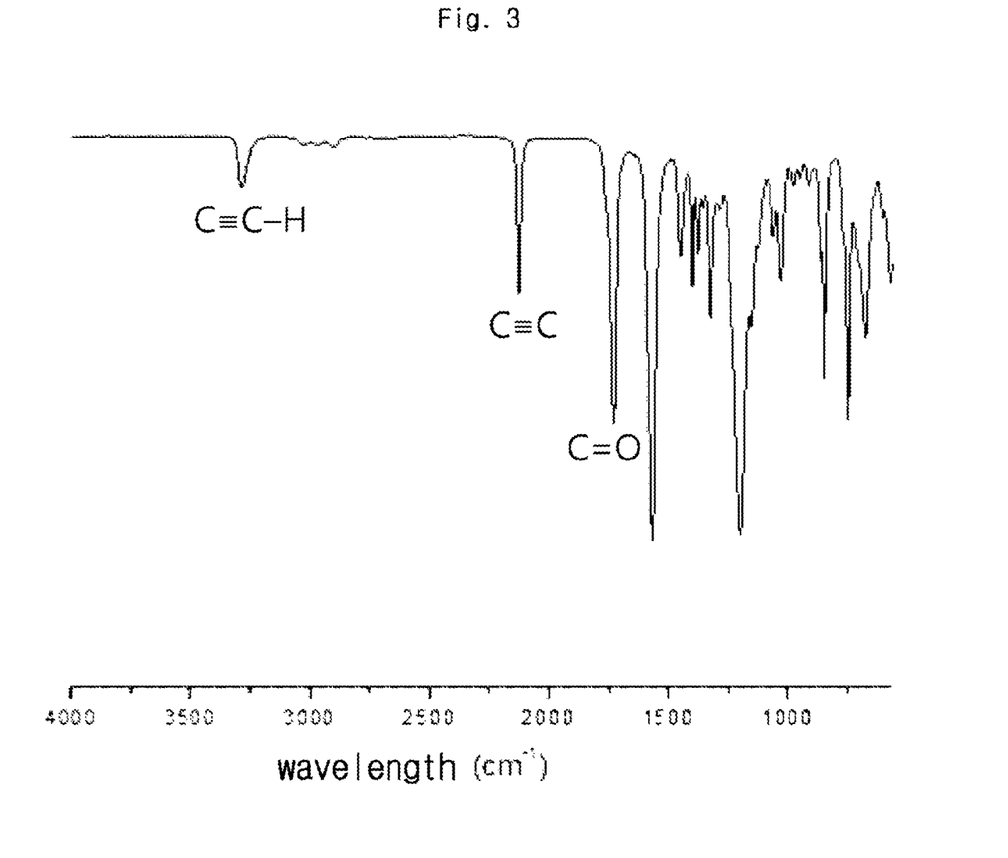
FIG. 3 is a plot showing the FT-IR spectroscopy result of DNPPE.

Further, from the FT-IR spectroscopy results as represented in FIG. 3 showing peaks indicating the presence of a nitro group (1500 cm$^{-1}$), a carbonyl group (C=O, 1650 cm$^{-1}$) and an acetylene group (2250 cm$^{-1}$), the synthesis of DNPPE was confirmed.

Figure 6:
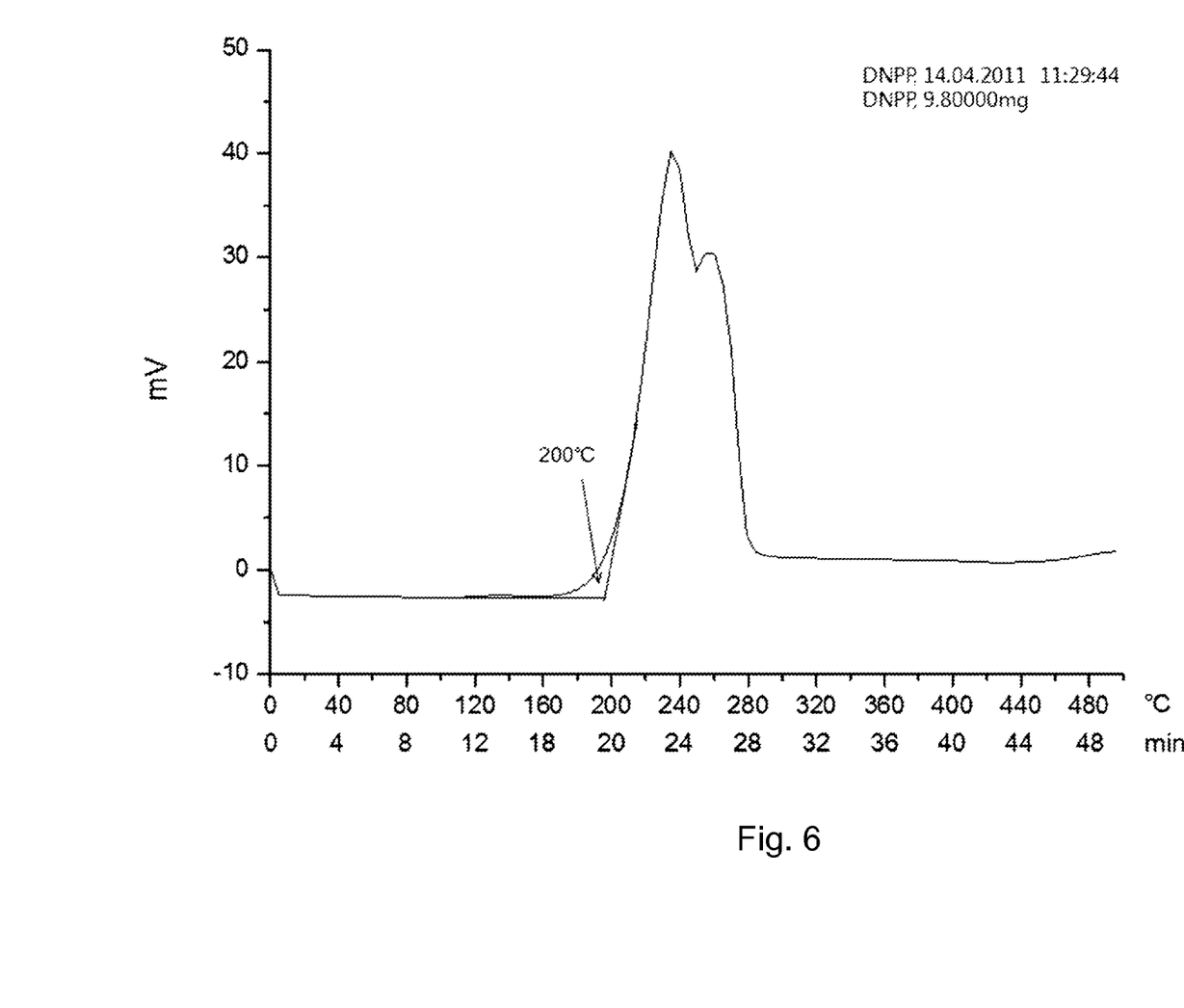
FIG. 6 is a plot showing the DSC result of DNPPE.

Thus synthesized DNPPE was purified by distillation, and the purity was determined as 84% by GC analysis. From the DSC analysis results as shown in FIG. 6, it was found that its degradation began at 200° C. and hit the maximal degradation at 220° C.

Preparation Example 2

Synthesis and analysis of 2,2-dinitropropyl-4-pentynoate (DNPPA)

An energetic reactive plasticizer, DNPPA was synthesized as shown in the following reaction scheme 3 via esterification reaction of DNP-OH and 4-pentynoic acid.

2,2-dinitropropyl-4-pentynoate 4-pentynoic acid (3 g, 30.6 mmol), DNP-OH (4.59 g, 30.6 mmol), 4-dimethylaminopyridine (DMAP) (1.03 g, 9.18 mmol) and 1-ethyl-3-(dimethylaminopropyl) carbodiimide hydrochloride (EDC.HCl) (6.45 g, 33.66 mmol) were placed into a 2-neck flask; then 26 ml dichloromethylene (MC) was further added thereto; and the mixture was stirred at room temperature for 4 hours. Solvent was removed from the reactants under reduced pressure, and the resultants were washed once with an aqueous solution of NaCl (10 wt %)/ethyl acetate and then washed 5 times with distilled water. Ethyl acetate was removed under reduced pressure and the resultant was distilled at 110° C. under high vacuum condition, resulting in DNPPA.

The conformation of thus synthesized DNPPA was identified by the following methods. Firstly, $^1$H-NMR spectrum was used to identify the molecular structure of DNPPA, resulting in: $^1$H NMR (CDCl$_3$, d, ppm): 2.01 (1H, 2.21 (3H, —CH$_3$), 2.51 (2H, —OOCCH$_2$_CH$_2$—), 2.62 (2H, —OOCCH$_2$_CH$_2$—) 4.96 (2H, —CH$_2$—COO—).

Figure 4:
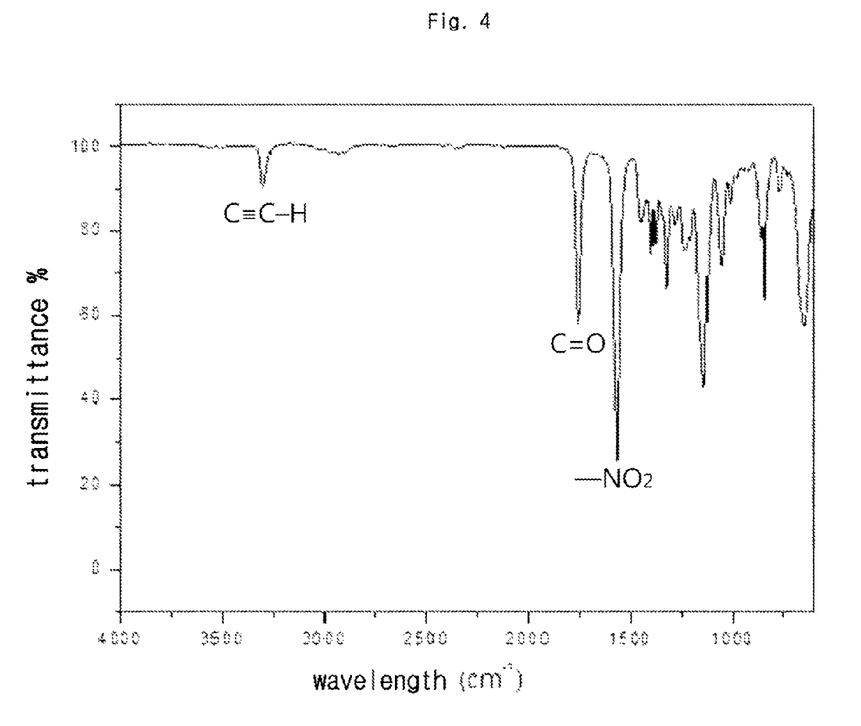
FIG. 4 is a plot showing the FT-IR spectroscopy result of DNPPA.

Further, from the FT-IR spectroscopy results as represented in FIG. 4 showing peaks indicating the presence of a nitro group (—NO$_2$, 1566 cm$^{-1}$), a carbonyl group (C=O, 1755 cm$^{-1}$) and an acetylene group (C—H, 3300 cm$^{-1}$), the synthesis of DNPPA was confirmed.

Preparation Example 3

Synthesis and analysis of 2,2-dinitropropyl-4-hexynoate (DNPHA)

An energetic reactive plasticizer, DNPHA was synthesized as shown in the following reaction scheme 4 via esterification reaction of DNP-OH and 5-hexynoic acid.

[Reaction scheme 4]

2,2-dinitropropyl-4-hexynoate 5-hexynoic acid (3.43 g, 30.6 mmol), DNP-OH (4.59 g, 30.6 mmol), 4-dimethylaminopyridine(DMAP) (1.03 g, 9.18 mmol) and 1-ethyl-3-(dimethylaminopropyl) carbodiimide hydrochloride (EDC.HCl) (6.45 g, 33.66 mmol) were placed into a 2-neck flask; then 27 ml dichloromethylene was further added thereto; and the mixture was stirred at room temperature for 4 hours. Solvent was removed from the reactants under reduced pressure, and the resultants were washed once with an aqueous solution of NaCl (10 wt %)/ethyl acetate and then washed 5 times with distilled water. Ethyl acetate was removed under reduced pressure and the resultant was distilled at 110° C. under high vacuum condition, resulting in DNPHA.

The conformation of thus synthesized DNPHA was identified by the following methods. Firstly, $^1$H-NMR spectrum was used to identify the molecular structure of DNPHA, resulting in: $^1$H NMR (CDCl$_3$, d, ppm): 2.00 (1H, C—H), 2.2 (3H, —CH$_3$), 2.55 (2H, —OOCCH$_2$_CH$_2$CH$_2$_), 1.85 (2H, —OOCCH$_2$_CH$_2$CH$_2$_), 2.27 (2H, —OOCCH$_2$_CH$_2$CH$_2$_) 4.92 (2H, —CH$_2$—COO—).

Figure 5:
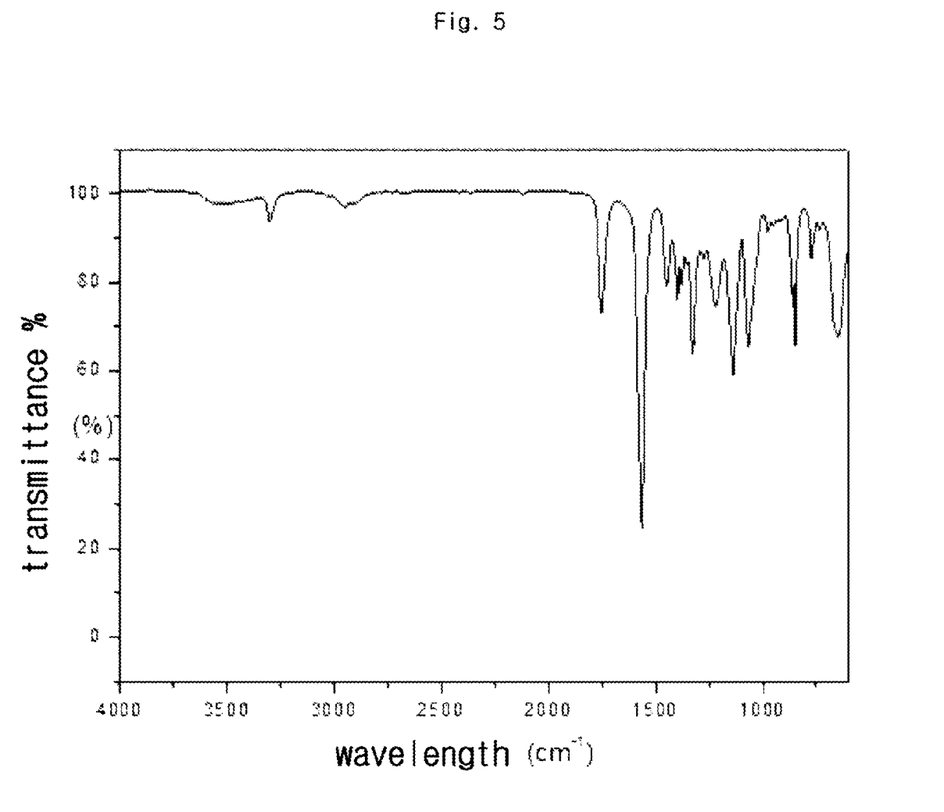
FIG. 5 is a plot showing the FT-IR spectroscopy result of DNPHA.

Further, from the FT-IR spectroscopy results as represented in FIG. 5 showing peaks indicating the presence of a nitro group (—NO$_2$, 1563 cm$^{-1}$), a carbonyl group (C=O, 1753 cm$^{-1}$) and an acetylene group (≡C—H, 3301 cm$^{-1}$), the synthesis of DNPHA was confirmed.

Example 1

Decrease in Viscosity of a Prepolymer Due to the Plasticizer

Figure 1:
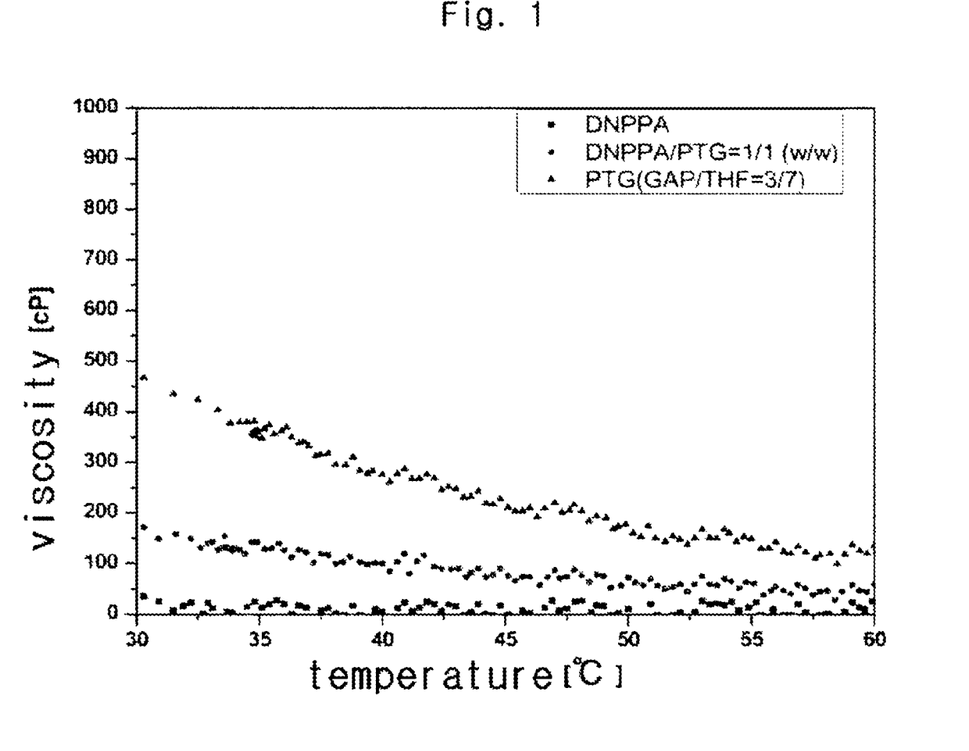
FIG. 1 is the results of viscosity test data for determining the availability of DNPPA as a plasticizer, showing viscosity changes of poly(GAP-co-THF) polyol prepolymer, prepared DNPPA and a mixture thereof (1:1 by weight), respectively.
Figure 2:
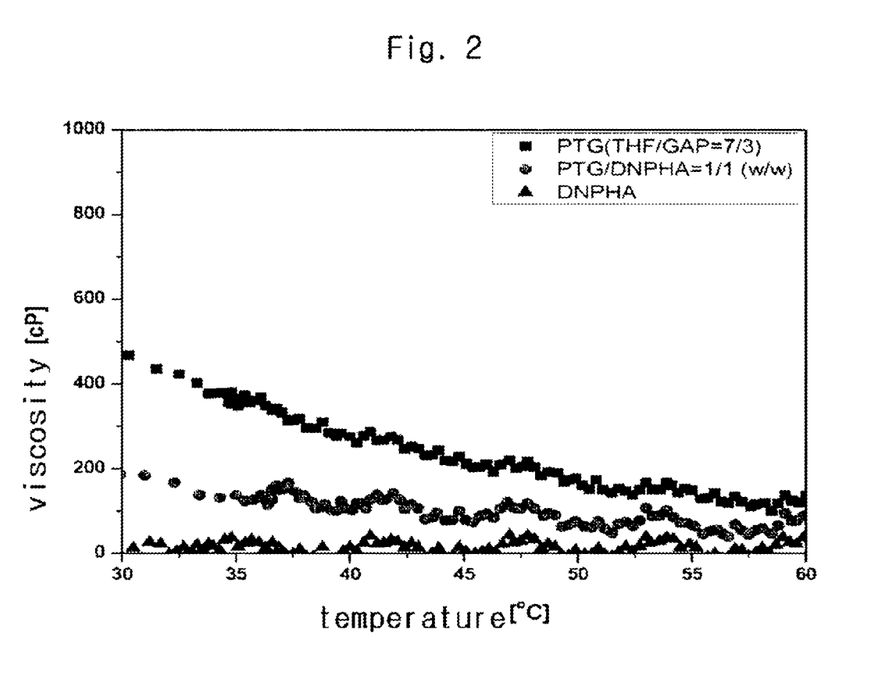
FIG. 2 is the results of viscosity test data for determining the availability of DNPHA as a plasticizer, showing viscosity changes of poly(GAP-co-THF) polyol prepolymer, prepared DNPHA and a mixture thereof (1:1 by weight), respectively.

For measuring viscosity, a viscometer, MCR 301 from Anton Paar Physica Co. was used by using a parallel plate having a 1 mm gap (CP25-1-SN9356, diameter=25 mm) at the temperature range of 30-60° C. at a constant shear rate of 1.0 s$^{-1}$ with a temperature elevation rate of 1° C./minutes. After measuring viscosity of a poly(GAP-co-THF) polyol prepolymer and the prepared plasticizer per se, viscosity of a mixture of the plasticizer and the poly(GAP-co-THF) polyol prepolymer (1:1 w/w) was measured, so as to determine the plasticization properties represented by the decrease in viscosity. The test results obtained from the cases wherein the above obtained plasticizer, DNPPA and DNPHA was applied respectively, were represented in FIGS. 1 and 2. As shown in FIGS. 1 and 2, as compared to viscosity of the poly(GAP-co-THF) polyol prepolymer, viscosity of a mixture of the plasticizer prepared according to the present invention and the poly(GAP-co-THF) polyol prepolymer was significantly lowered, over the whole temperature range measured, thereby showing the significant plasticizing effect of the synthesized plasticizer according to the present invention.

INDUSTRIAL APPLICABILITY

The energetic reactive plasticizer according to the present invention is designed to be present in a form bound to the polymeric binder through covalent bond with the branch of the polymeric backbone of polymeric binder during a curing process, so as to prevent a conventional migration or exudation problem of an energetic plasticizer from the molded plastic PBX, while ensuring the essential physical properties required in an energetic plasticizer used in plastic PBX preparation, such as increased energy density and enhanced processability by lowered viscosity in a blending process.

When the energetic reactive plasticizer according to the present invention is applied to the plastic PBX preparation, the conventional plasticizer migration problem from plastic PBX can be prevented, leading to further advantageous effects such as an improvement in long term storage property of PBX and energy density increase in the whole composition.

The invention claimed is:
1. A reactive plasticizer comprising an ester compound represented by the following chemical formula:

wherein n is a natural number of 1 to 10.

2. The reactive plasticizer according to claim 1, wherein the ester compound is 2,2-dinitropropyl-4-pentynoate or 2,2-dinitropropyl-5-hexynoate.

* * * * *